US012712086B2

(12) United States Patent
Singh

(10) Patent No.: US 12,712,086 B2
(45) **Date of Patent: *Aug. 18, 2026**

(54) SYSTEMS AND METHODS FOR CONTAGIOUS ILLNESS SURVEILLANCE AND OUTBREAK DETECTION

(71) Applicant: KINSA HEALTH, LLC, Miami, FL (US)

(72) Inventor: Inder Raj Singh, San Francisco, CA (US)

(73) Assignee: Kinsa Health, LLC, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/893,297

(22) Filed: Sep. 23, 2024

(65) Prior Publication Data

US 2025/0087373 A1 Mar. 13, 2025

Related U.S. Application Data

(63) Continuation of application No. 18/220,897, filed on Jul. 12, 2023, now Pat. No. 12,125,597, which is a continuation of application No. 17/708,314, filed on Mar. 30, 2022, now Pat. No. 11,715,568, which is a continuation of application No. 17/156,810, filed on Jan. 25, 2021, now Pat. No. 11,309,091.

(60) Provisional application No. 63/082,288, filed on Sep. 23, 2020, provisional application No. 62/991,074, filed on Mar. 18, 2020, provisional application No. 62/991,472, filed on Mar. 18, 2020.

(51) Int. Cl.

| | |
|---|---|
| ***G06F 16/29*** | (2019.01) |
| ***G01K 13/20*** | (2021.01) |
| ***G16H 50/80*** | (2018.01) |
| ***G16H 80/00*** | (2018.01) |

(52) U.S. Cl.

CPC ............. *G16H 50/80* (2018.01); *G01K 13/20* (2021.01); *G06F 16/29* (2019.01); *G16H 80/00* (2018.01)

(58) Field of Classification Search

CPC ......... G16H 50/80; G01K 13/20; G06F 16/29

See application file for complete search history.

(56) References Cited

U.S. PATENT DOCUMENTS

| | | | |
|---|---|---|---|
| 3,241,370 | A | 3/1966 | Mertler et al. |
| 3,872,728 | A | 3/1975 | Joyce et al. |
| 3,906,796 | A | 9/1975 | Dumbeck |
| 4,031,365 | A | 6/1977 | Raggiotti et al. |
| 4,041,382 | A | 8/1977 | Washburn |

(Continued)

OTHER PUBLICATIONS

International Search Report and Written Opinion of the International Searching Authority, issued in International Application No. PCT/US2021/020573; Jun. 1, 2021; 9 pages.

(Continued)

*Primary Examiner* — Reginald R Reyes

(74) *Attorney, Agent, or Firm* — Woods Oviatt Gilman LLP; David Groesbeck

(57) ABSTRACT

Systems and methods for population health surveillance utilizing a network of smart thermometers is provided. Based on the geolocated user data provided by the smart thermometers, contagious illness can be forecasted for various population nodes. Population nodes can be provided at various levels of granularity. Geographic or population specific early warning signals can be generated based on detected outbreaks of contagious illness.

20 Claims, 10 Drawing Sheets

(56) References Cited

U.S. PATENT DOCUMENTS 4,321,933 A 3/1982 Baessler
4,392,782 A 7/1983 Kuehn, III et al.
4,422,066 A 12/1983 Belcourt et al.
4,475,823 A 10/1984 Stone
5,050,430 A 9/1991 Begin et al.
6,234,964 B1 5/2001 Iliff
6,440,069 B1 8/2002 Raymond et al.
6,579,231 B1 6/2003 Phipps
6,839,651 B2 1/2005 Lantz et al.
6,925,324 B2 8/2005 Shusterman
7,293,915 B2 11/2007 Chen
7,870,249 B2 1/2011 Brown
7,946,996 B2 5/2011 Callister et al.
8,335,298 B2 12/2012 Clawson
8,548,828 B1 10/2013 Longmire
8,556,503 B2 10/2013 Tseng
8,577,642 B2 11/2013 Pompei et al.
8,974,115 B2 3/2015 Segal et al.
9,075,909 B2 7/2015 Almogy et al.
9,593,985 B2 3/2017 Segal et al.
2003/0002562 A1 1/2003 Yerlikaya et al.
2003/0214999 A1 11/2003 Chapman et al.
2004/0073459 A1 4/2004 Barthell
2004/0103010 A1 5/2004 Wahlbin et al.
2006/0036619 A1 2/2006 Fuerst et al.
2006/0178567 A1 8/2006 Goh et al.
2007/0185397 A1 8/2007 Govari et al.
2007/0229290 A1 10/2007 Kahn et al.
2008/0103370 A1 5/2008 Dicks et al.
2008/0177571 A1 7/2008 Rooney et al.
2008/0200774 A1 8/2008 Luo
2008/0221930 A1 9/2008 Wekell et al.
2008/0269571 A1 10/2008 Brown et al.
2009/0234916 A1 9/2009 Cosentino et al.
2010/0039288 A1 2/2010 Mitchell et al.
2010/0308980 A1 12/2010 Gosset et al.
2010/0314443 A1 12/2010 Cudzilo
2011/0064231 A1 3/2011 Goldberg et al.
2011/0093249 A1* 4/2011 Holmes .................. G16Z 99/00
703/6
2011/0098966 A1 4/2011 Suzuki
2011/0252003 A1 10/2011 Mitchell et al.
2011/0270631 A1 11/2011 Cambray et al.
2012/0099617 A1 4/2012 Tseng
2012/0112883 A1 5/2012 Wallace et al.
2012/0116184 A1 5/2012 Shieh
2012/0220835 A1 8/2012 Chung
2012/0226771 A1 9/2012 Harrington et al.
2012/0244886 A1 9/2012 Blom et al.
2012/0290266 A1 11/2012 Jain et al.
2013/0132572 A1 5/2013 Pan
2013/0179195 A1 7/2013 Lorsch
2013/0318027 A1 11/2013 Almogy et al.
2014/0086277 A1 3/2014 Sanchez et al.
2014/0086278 A1 3/2014 Welland
2014/0108374 A1 4/2014 Dodge et al.
2014/0155708 A1 6/2014 Petersen et al.
2014/0216136 A1 8/2014 Yim
2014/0243637 A1 8/2014 Rahman et al.
2015/0100330 A1 4/2015 Shpits
2015/0272195 A1 10/2015 Hyde et al.
2015/0317445 A1 11/2015 Singh et al.
2016/0019344 A1 1/2016 Singh et al.
2016/0026768 A1 1/2016 Singh et al.
2016/0027278 A1 1/2016 Mcintosh et al.
2016/0113569 A1* 4/2016 Zhao .................. A61B 5/6898
600/300
2017/0017759 A1 1/2017 MacNeice et al.
2017/0061074 A1* 3/2017 Singh .................... G16H 10/60
2018/0058939 A1 3/2018 Pompei et al.
2018/0107793 A1 4/2018 Ni et al.
2018/0350455 A1 12/2018 Rosen
2020/0118665 A1 4/2020 Bender et al.

OTHER PUBLICATIONS

Extended European Search Report Written Opinion for corresponding European Patent Application No. 21771815.4 issued Mar. 27, 2024, 8 pages.

* cited by examiner

602 Over a period of time receive user data from each of the mobile computing devices via network communications. The user data received from each of the computing devices comprises a geolocation of the computing device, a user temperature reading as collected by the associated temperature sensing probe, and a time stamp associated with the temperature reading 604 For each of the plurality of different geographic regions, based on the user data received from the mobile computing devices physically located within each of the different geographic regions, determine a rate of change of fever-induced illness based on the user data received from the mobile computing devices physically located within each of the different geographic regions over the period of time 606 Generate an illness signal for each of the different geographic regions based on the determined rate of change of fever-induced illness for each of the different geographic regions 608 Graphically convey the illness signal for each of the different geographic regions, and wherein the illness signal is a real-time illness signal

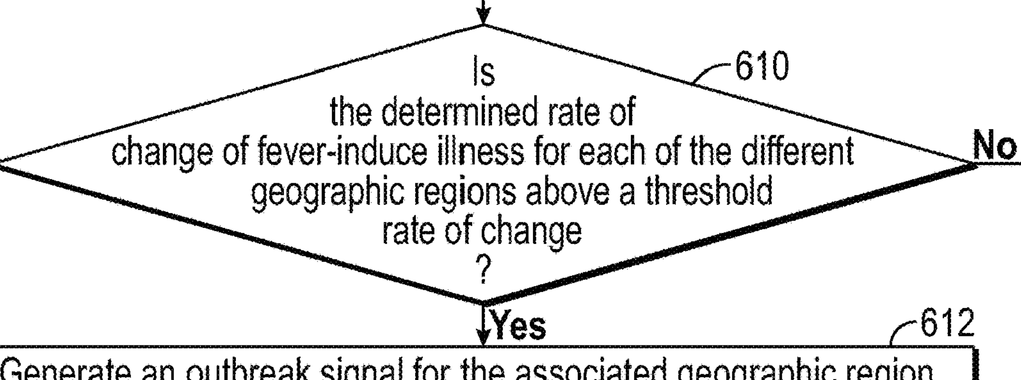

612 Generate an outbreak signal for the associated geographic region

614 Determine an effective reproduction rate (rt) for each of the different geographic regions based at least in part on the determined rate of change of fever-induced illness for each of the different geographic regions

FIG. 10

SYSTEMS AND METHODS FOR CONTAGIOUS ILLNESS SURVEILLANCE AND OUTBREAK DETECTION

CROSS-REFERENCE TO RELATED APPLICATIONS

This application is a continuation of U.S. patent application Ser. No. 18/220,897, filed Jul. 12, 2023, and issued as U.S. Pat. No. 12,125,597, which is a continuation of U.S. patent application Ser. No. 17/708,314, filed on Mar. 30, 2022, and issued as U.S. Pat. No. 11,715,568, which is a continuation of U.S. patent application Ser. No. 17/156,810 filed on Jan. 25, 2021 and issued as U.S. Pat. No. 11,309, 091, which claims priority to U.S. patent application Ser. No. 62/991,074 filed on Mar. 18, 2020; U.S. patent application Ser. No. 62/991,472 filed on Mar. 18, 2020; and U.S. patent application Ser. No. 63/082,288 filed on Sep. 23, 2020 the disclosures of which are each incorporated herein by reference in their entirety.

BACKGROUND

Infectious diseases continue to be one of the greatest public health concerns across the globe. The economic burden of seasonal influenza amounts to $87.1 billion each year in the United States alone, despite widespread public attention and the billions invested in preventative measures. The United States and other countries, however, lack reliable signals to rapidly identify developing infectious disease hotspots. The Centers for Disease Control and Prevention (CDC) uses two major systems for epidemic surveillance: (1) the National Notifiable Diseases Surveillance System (NNDSS), through which local and state health departments send CDC data for about 120 diseases that are predominantly diagnosed via laboratory confirmation; by definition, this is unable to detect novel illnesses outside of the diseases routinely sent and is a lagging indicator due to reliance on existing testing infrastructure, and (2) ILI-Net (with COVID-19-Like Illness, or CLI, tracking), which is based on outpatient tracking, so is delayed by reporting lags and biased by changes in care-seeking behavior and differentiated access to care. Additionally, outpatient tracking only captures patients who engaged with the healthcare system, potentially missing the vast number of patients with mild or asymptomatic cases. Not only lagging and incomplete, these metrics also vary across 50 states, creating blind spots for leaders who are making decisions that affect millions of people. Thus, while various entities provide modeling and forecasting for influenza-like illness (ILI), such ILI forecasts typically have a lead time of less than 4 weeks, often do not include geographic granularity, and are based on lagging data sets. Further, even in view of an accurate ILI forecast, the unpredictable threat of epidemic or pandemic illnesses, such as COVID-19, or the rapid emergence or re-emergence of diseases like Zika and Ebola are often difficult to quickly identify and target to allow for rapid response and intervention.

BRIEF DESCRIPTION OF THE DRAWINGS

It is believed that certain embodiments will be better understood from the following description taken in conjunction with the accompanying drawings, in which like references indicate similar elements and in which:

FIG. 10 is a flow chart of an example process that can be performed by an illness detection and tracking computing system in accordance with one non-limiting embodiment.

DETAILED DESCRIPTION

Figure 1:
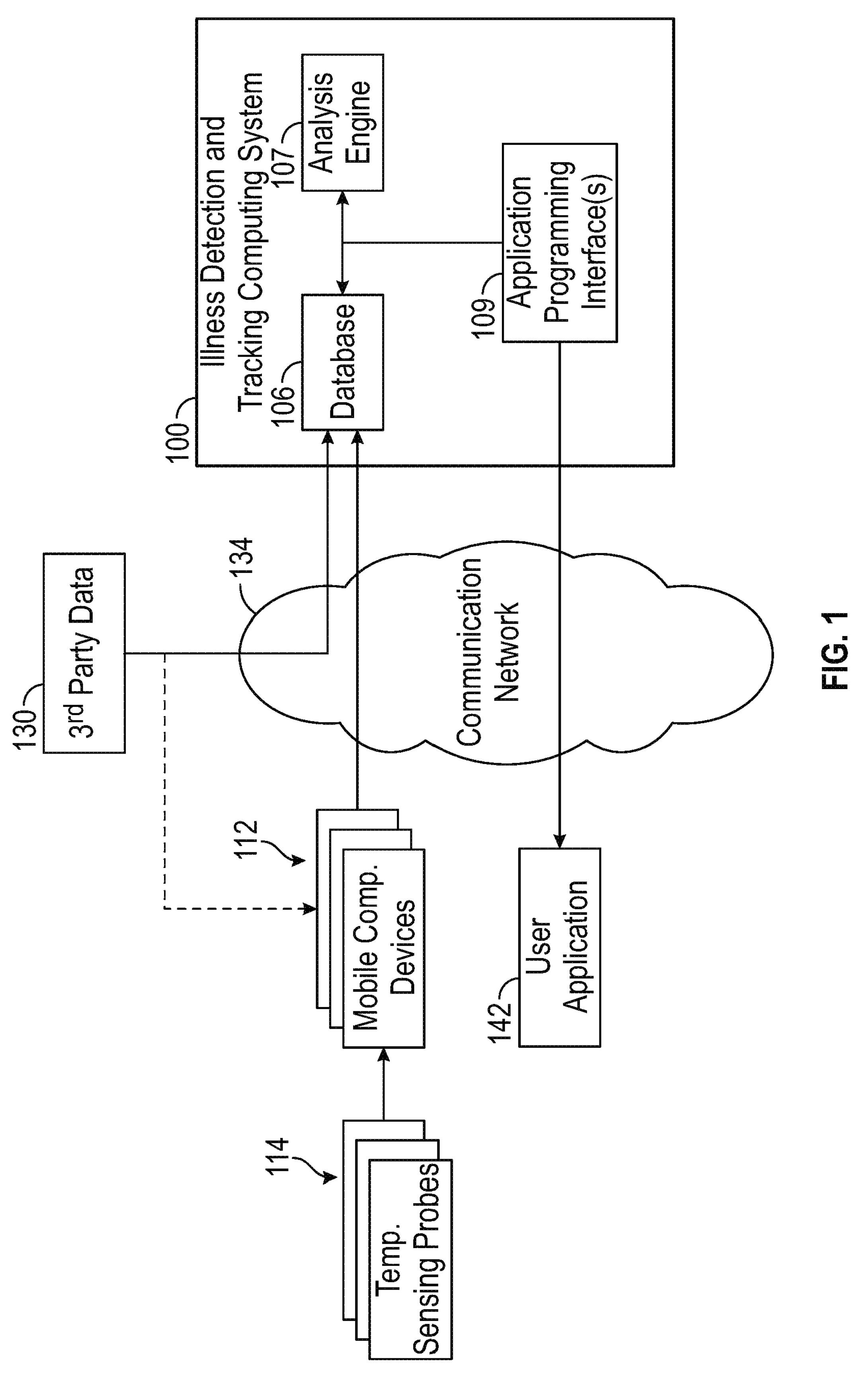
FIG. 1 schematically illustrates an end-to-end illness data collection and processing system in accordance with one non-limiting embodiment.

Various non-limiting embodiments of the present disclosure will now be described to provide an overall understanding of the principles of the structure, function, and use of systems, apparatuses, devices, and methods disclosed. One or more examples of these non-limiting embodiments are illustrated in the selected examples disclosed and described in detail with reference made to FIGS. 1-10 in the accompanying drawings. Those of ordinary skill in the art will understand that systems, apparatuses, devices, and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

The systems, apparatuses, devices, and methods disclosed herein are described in detail by way of examples and with reference to the figures. The examples discussed herein are examples only and are provided to assist in the explanation of the apparatuses, devices, systems and methods described herein. None of the features or components shown in the drawings or discussed below should be taken as mandatory for any specific implementation of any of these apparatuses, devices, systems or methods unless specifically designated as mandatory. For ease of reading and clarity, certain components, modules, or methods may be described solely in connection with a specific figure. In this disclosure, any identification of specific techniques, arrangements, etc. are either related to a specific example presented or are merely a general description of such a technique, arrangement, etc. Identification of specific details or examples are not intended to be, and should not be, construed as mandatory or limiting unless specifically designated as such. Any failure to specifically describe a combination or sub-combination of components should not be understood as an indication that any combination or sub-combination is not possible. It will be appreciated that modifications to disclosed and described examples, arrangements, configurations, components, elements, apparatuses, devices, systems, methods, etc. can be made and may be desired for a specific application. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented, but instead may be performed in a different order or in parallel.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

In accordance with various embodiments of the present disclosure, user data obtained from a network of temperature sensing probes (sometimes referred to as "smart thermometers") can be leveraged to identify increased transmission and growth in the number of people that are sick. In some cases, the network of temperature sensing probes includes hundreds of thousands, or even millions, of temperature sensing probes that are each collecting user data from various geographic regions or other types of population nodes. Beneficially, due to the minimization of lag between the data collection and processing, as well as the massive volume of user data received from the network of temperature sensing probes, such identification of increased transmission and/or growth can occur well before the established healthcare system could even potentially detect similar metrics.

By way of explanation, the healthcare system does not gain data from mildly symptomatic people who never go to a doctor, hospital, or a lab because their symptoms are treatable at home or resolve without requiring medical attention. Furthermore, underserved populations may be less likely to visit a doctor, a hospital, or a lab for mild or even more severe illness due to cost of care and barriers to accessing care. Underserved populations are often at an increased risk of experiencing infectious disease due to factors such as more crowded living conditions, higher contact-intensity jobs, and more limited access to healthcare resources. The presently disclosed systems and methods are able to ingest data from these underserved communities which are underrepresented up by current healthcare data. Moreover, conventional healthcare data is too delayed to provide similar insights as provided by the systems and methods described herein, since by the time the healthcare system identifies an anomaly of infectious disease cases, especially of initially unknown origin such as COVID-19, the associated outbreak is already occurring on a large scale and the time period in which actions would have needed to be taken to minimize the effects of the outbreak has passed.

Furthermore, in accordance with the systems and methods described herein, not every user must have a particular symptom in order for the network of temperature sensing probes to see and identify the spread of illness. By way of example, even if only a fraction of users have symptoms (such as a fever, for example), the network of temperature sensing probes can still pick up on the growth in that number of people to correctly assess transmission rates. Thus, if only 50% of people with COVID-19, for example, have a fever, but the user data received from the network of temperature sensing probes indicates that the number of people in a particular geography doubles, it can be determined that COVID-19 is spreading. The transmission rate can also be assessed and reported based on the user data received from the network of temperature sensing probes.

As described in more detail below, various embodiments of the present disclosure also generally relate to long-lead ILI forecasting based on real-time data collected from the network of temperature sensing probes. In some embodiments, for example, a 12-week ILI forecast can be generated for a particular geographic area based on geo-coded data collected from smart thermometers within the network, as described in more detail below. Long-lead ILI forecasting in accordance with the present disclosure can leverage geo-specific data to estimate the seasonal transmissivity of flu per city, or other type of geographic region or population node (such as a school, workplace, or other suitable grouping of users), allowing an influenza transmission fingerprint to be developed for each geographic area, based on past influenza outbreaks. Geographic areas can have unique epidemic intensity curves driven by climate and population structure and these patterns can be used to build highly accurate long-lead ILI forecasts for geo-specific regions. Forecasts described herein can leverage multiple years of county-specific incidence data to calculate daily reproductive number (R) estimates that are unique to each geographic area using the Equation (1):

$$I_{t+1} = R_t \sum_k w_k I_{t-k} \qquad (1)$$

where w is the generation distribution time, I is county-level incidence (as detected by an illness detecting and tracking computing system 100 of FIG. 1, described below), R is the reproductive number, and $\Sigma_k W_k I_{t-k}$ is effective incidence. Further, w can be estimated based on findings from literature on the rates of flu spread using a gamma distribution for spread from hosts for 1 to 5 days, with a mean of 2.5 days and scale of 0.6 days, for example.

Using Equation (1), R can be estimated for all previous daily timesteps per region and then median R per day of year can be estimated. This approach can provide an influenza transmission fingerprint per locale that can be used to predict future influenza incidence by forward propagating I using the same equation above. For forward prediction, the daily estimates of R can be substituted for all future dates (t) to predict $I_{t+1}$. Finally, measurement uncertainty in the incidence and influenza predictions can be accounted for by running an ensemble of predictions where random Gaussian noise is added to the starting values of/at the point of influenza forecasting. The scale of Gaussian noise can be determined for each geographic area by estimating the standard deviation of measurement noise for each geographic area via detrending the incidence time-series with a 14-day centered rolling mean. The noise observed in the incidence signal is normally distributed and decreases with the number of temperature sensing probes per geographic area.

FIG. 1 schematically illustrates an end-to-end illness data collection and processing system in accordance with one non-limiting embodiment. Such illness data can be utilized to generate long-lead ILI forecasts, outbreak detection, and provide other illness-related signaling in accordance with the present disclosure. More specifically, the system can allow for data collection from individuals immediately from symptom onset, such as via a smart thermometer, a consistently used symptom tracking mobile app, a wearable device, and/or other data acquisition approaches. The system can thereby acquire key illness biometric/vital sign data such as without limitation, temperature, heart rate, and/or respiratory rate, alongside GPS level coordinates. Via symptom or biometric illness data, the system can detect illness earlier in the course of disease than traditional surveillance mechanisms, since the system can detect illness around symptom onset as opposed to the delay of having an individual with worsening symptoms deciding to seek care, being able to access that care and diagnostic testing, and the lag of running and reporting test results. Widespread use of the system by disparate populations, but especially key sentinel populations that are frequently among the first impacted by infectious disease spread due to exposures at school, work or home (e.g., children, underserved communities, larger multi-generation households, front line workers and first responders) can beneficially increase accuracy and robustness of the system output.

By way of example, if atypical illness is detected amongst those sentinel groups that are providing symptomatic or biometric illness data, and is detected earlier than through traditional surveillance mechanisms due to the nature of the system, a potential outbreak can be detected at its early stages before further community spread takes place. In contrast, due to the lagging nature of care seeking and diagnostic testing, when existing traditional disease surveillance systems are used, once atypical levels of illness are detected via laboratory testing from individuals who sought care, sufficient time has passed for more widespread disease transmission to occur. Due to the exponential nature of infectious disease transmission, a difference in detection and response time on the magnitude of days can have significant ramifications on reducing morbidity, mortality and societal cost of disease. In accordance with various embodiments, the system can leverage multiple types of data inputs, such as multiple biometric data inputs (temperature, heart rate, respiratory rate, and so forth) as well as symptom inputs. Those data inputs, coupled with knowing which family member (for calculation of household transmission) provided the data and growth in nodes (e.g., schools) yields an optimal system for detection of outbreaks, forecasting and differentiation from normal/seasonal epidemics.

The system can comprise, for example, a plurality of temperature sensing probes 114 (such as medical thermometers) that are each communicatively coupled with a respective auxiliary computing device, such as mobile computing devices 112 (e.g. smartphones, tablets, computers, and so forth). The mobile computing devices 112 can be coupled with an illness detection and tracking computing system 100 through a communication network 134. While FIG. 1 and other figures herein depict the use of temperature sensing probes, this disclosure is not so limited. Instead, the systems and methods described herein are operable using data collected by any of a variety of biometric collection devices. Thus, while many operational embodiments are described in the context of temperature-based data collected by a thermometer, other embodiments can utilize data from other types of biometric collection devices, such as, without limitation, pulse oximeters, heart rate monitors, wearable fitness trackers or other types of wearables, and the like. Many such biometric collection devices can be utilized by users prior to entering the healthcare system (i.e., prior to a doctor's appointment or hospital visit), thereby providing timely biometric data to the illness detecting and tracking computing system 100 that would not otherwise be available, or would necessarily be lagging data.

In some embodiments, a user can provide various data related to the user's health into to the mobile computing devices 112, for example, symptoms, medications taken, vaccinations, or diagnoses. By way of example, users can set up a profile with additional contextual data associated with each profile, such as the age of the user, gender, school, employer, and other social and demographic data that would inform the user's risk of acquiring specific illnesses or for treatment recommendations. The profile can be used, for example, to associate the user with one or more different population nodes. Multiple profiles can be created per mobile computing device 112. In some embodiments, users may indicate that specific profiles belong to the same household or other social group.

Additionally or alternatively, the mobile computing device 112 can be leveraged to collect various biometric data from its user. By way of example, heart rate detection can be provided by the mobile computing device 112. In some embodiments, the mobile computing device 112 can provide respiratory rate, or other respiratory-related information to the illness detecting and tracking computing system 100. Any of a variety of suitable approaches can be used to track heart rate, respiratory rate, or other biometric data using the mobile computing device 112, such as using an on-board camera, microphone, or one or more specialized biometric sensors.

User data, such as temperature readings and/or other biometric data, and in some cases user-entered health information, can be transmitted to the illness detection and tracking computing system 100 by the mobile computing device 112. In some cases, temperature sensing probes 114 can be configured to transmit data directly to the illness detection and tracking computing system 100 without the aid of the mobile computing device 112. In yet other embodiments, the user may manually enter temperature data directly into the mobile computing device 112 (i.e., via a touchscreen interface) that is, in turn, transmitted to the illness detection and tracking computing system 100. In any event, the illness detection and tracking computing system 100 can be configured to store various types of data transmitted from the mobile computing device 112 or the temperature sensing probe 114 in one or more databases 106. The mobile computing device 112 can be further configured to transmit to the illness detection and tracking computing system 100 one or more geolocations (e.g., latitude, longitude coordinates), IP addresses, and one or more time measurements. The geolocations can identify the location of the individual when taking a temperature or recording symptoms, thereby allowing for geographic granularity. The time measurements can include the time when the individual was taking a temperature or recording symptoms.

In some embodiments, the illness detection and tracking computing system 100 can retrieve other data sets, shown as third party data 130, which are not generated by the temperature sensing probes 114. For example, the illness detection and tracking computing system 100 can retrieve web data from the Centers for Disease Control's (CDC's) Weekly U.S. Influenza Surveillance Report, for the purpose of training machine learning models that identify illness features that distinguish influenza from other fever-inducing illnesses.

In accordance with the present disclosure, raw data collected by the illness detection and tracking computing system 100 can be transformed by an analysis engine 107 into illness signals. In one embodiment, these illness signals are made available for consumption by external applications or organizations (e.g., public health system) through application programming interfaces (APIs) 109 accessed by a user application 142. In one embodiment, the illness detection and tracking computing system 100 can produce a signal indicative of aggregated community influenza levels for particular geographic areas, for example. Such signal can be used to generate the long-lead ILI forecasting models, as well as used to generate outbreak detection and tracking, as described herein.

While influenza forecasting models can be helpful, rapid identification of emerging epidemics remains a massive challenge. In accordance with the present disclosure, however, systems and methods are provided to detect for localized illness anomalies for a population node, census track, census block, or other geographic region based on the real-time incidence data collected by the illness detection and tracking computing system 100 (FIG. 1). Additionally or alternatively, ILI forecasting models can be used to estimate expected illness trends by making predictions prior to an expected outbreak of illnesses such as COVID-19, H1N1, SARS, MERS, and so forth. In accordance with some embodiments of the present disclosure, the real-time signal generated by the illness detection and tracking computing system 100 can be compared to the expectations of the ILI model for a particular geographic area or other type of population node. Illness trends that are not likely due to normal seasonal influenza patterns can be identified such that further investigation into the anomalous data can be initiated. Thus, real-time illness levels in a particular population node (i.e., geographic region, city, county, state, school, school system, workplace, etc.), as detected by the illness detection and tracking computing system 100 can be compared to the ensemble predictions of expected influenza. Such comparison can be used to estimate the likelihood that currently detected incidences are due to seasonal influenza dynamics. In some embodiments, any real-time value above an upper 95% confidence interval of seasonal influenza can be flagged as anomalous. Additionally or alternatively, other characteristics of the real-time illness levels can be assessed by the illness detection and tracking computing system 100 to identify potential infectious disease hotspots. For example, when a rate of users with a fever increases above a threshold rate, the population node associated with those users can be flagged as anomalous. In some embodiments, a threshold may be determined by calculating the level of expected illness if it were dispersed equally over a population. If a certain sub-population node exceeds that level, it can be flagged as anomalous. Other approaches for determining suitable thresholds can be deployed without departing from the scope of the present disclosure.

Figure 2:
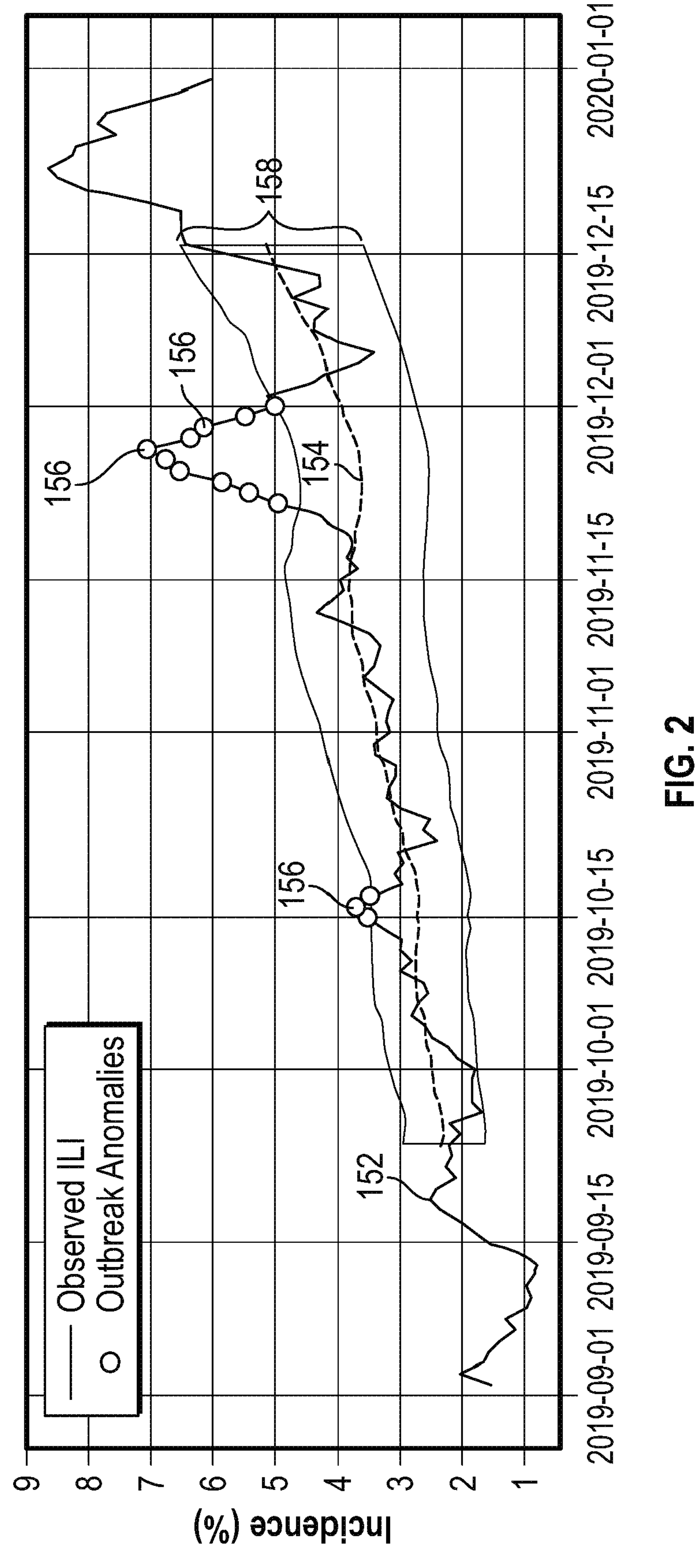
FIG. 2 depicts a plot showing observed influenza-like illnesses for a geographic area based on the real-time data collected by the illness detection and tracking computing system of FIG. 1.

Referring now to FIG. 2, a plot 150 is provided that shows observed influenza-like illnesses 152 for a particular population node based on the real-time data collected by the illness detection and tracking computing system 100 (FIG. 1). The population node can be, for example, a geographic area. An influenza forecast 154 on the plot 150 is the median of the expected influenza forecast, and the band 158 represents upper and lower 95% confidence intervals. As is to be appreciated, any suitable confidence intervals can be used. The influenza forecast 154 can be a long-lead ILI forecast generated in accordance with the present disclosure, or it can be an ILI forecast generated by a third party. The plot 150 shows numerous outbreak anomalies 156 based on the user data collected from a network of temperature sensing probes, each of which exceeds the upper 95% confidence interval. Once the outbreak anomalies 156 are detected, the illness detection and tracking computing system 100 can flag the incidences for further investigation using any suitable notification or alerting approach. In one embodiment, illness signals based on the outbreak anomalies 156 can be made available for consumption by external applications or organizations. Examples of signals produced can include, without limitation, illness incidence, illness prevalence for a population, effective transmission rates, among others.

In accordance with the presently disclosed systems and methods, a variety of visualizations, dashboards, animations, among other types of displays can be generated to convey information regarding ILI forecasts, outbreak anomalies, and so forth. In some embodiments, the illness detection and tracking computing system 100 is configured to generate such displays, although this disclosure is not so limited. Such information can be displayed based on real-time data, or substantially real-time data (i.e., daily), such as based on the signals generated by the illness detection and tracking computing system 100.

Figure 3:
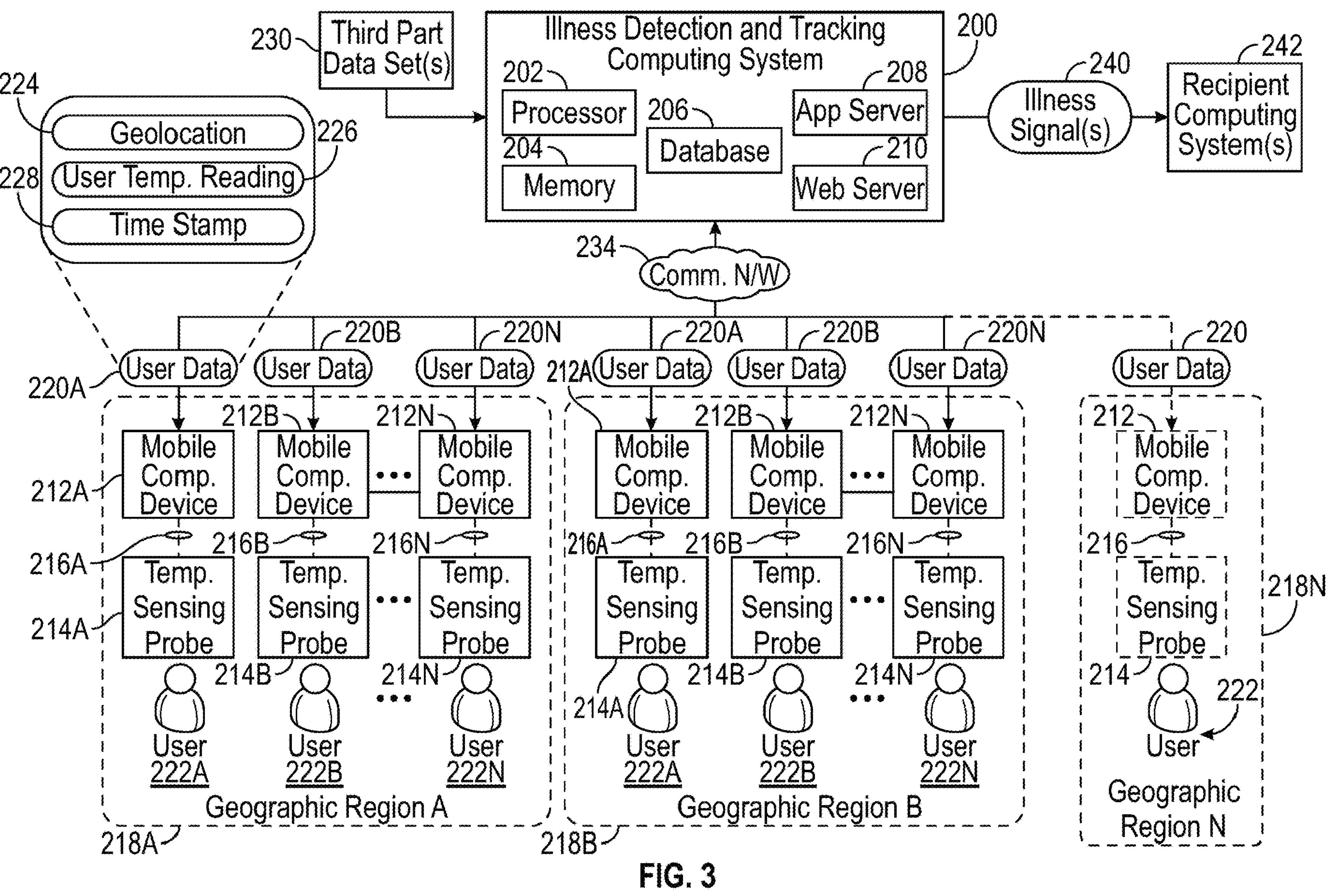
FIGS. 3-4 depict example illness detection and tracking computing systems in accordance with various non-limiting embodiments.

Referring now to FIG. 3, another example illness detection and tracking computing system 200 is depicted. The illness detection and tracking computing system 200 is shown in communication with a plurality of mobile computing devices 212A-N that are members of various population nodes. In the illustrated example, the population nodes are illustrated as geographic regions 218A-N. Additionally or alternatively, in other examples the plurality of mobile computing devices 212A-N can each be associated with a particular school, school system, campus, workplace, or other environment, grouping, or collection.

As shown in FIG. 3, each mobile computing device 212A-N can be communicatively coupled to an associated temperature sensing probe 214A-N via communications 216A-N. For example, in some embodiments, the communications 216A-N utilize a Bluetooth® communications protocol, although this disclosure is not so limited, as any of a variety of wired or wireless communications 216A-N can be utilized. Each temperature sensing probe 214A-N can be associated with a user 222A-N, respectively. While FIG. 3 depicts the use of data collected by temperature sensing probe 214A-N this disclosure is not so limited. As provided above, any suitable type of biometric collection device can be used without departing from the scope of the current disclosure.

The example geographic regions 218A-N of FIG. 3 can be any suitable region, such as a county, a zip code, a state, a country, a metropolitan statistical area (MSA), among any other suitable demarcation. Further, each of the various geographic regions 218A-N can be formed from different types of boundaries. For example, the geographic region 218A can be a city while the geographic region 218B can be a county. In any event, a plurality of temperature sensing probes 214A-N can be actively collecting temperatures of the users 222A-N within the various geographic regions 218A-N. In some use cases, each the geographic regions 218A-N can include thousands and thousands of temperature sensing probes 214A-N. Larger sized geographic regions 218A-N may include hundreds of thousands, or even millions, of temperature sensing probes 214A-N. Furthermore, as provided above, while FIG. 3 illustrates population nodes in the context of geographic regions, the presently disclosed systems and methods can provide the functionality to group the users 222A-N into any of a number of different population nodes.

In some embodiments, and similar to the system of FIG. 1, mobile communication devices 212A-N can be in communication with the illness detection and tracking computing system 200 via any suitable communication network 234. The communication network 234 can include any suitable computer or data networks, including the Internet, LANs, WANs, GPRS networks, etc., that can comprise wired and/or wireless communication links.

The mobile communication devices 212A-N can be any type of computer device suitable for communication with the illness detection and tracking computing system 200 over the communication network 234, such as a wearable computing device, a mobile telephone, a tablet computer, a device that is a combination handheld computer and mobile telephone (sometimes referred to as a "smart phone"), a personal computer (such as a laptop computer, netbook computer, desktop computer, and so forth), or any other suitable mobile communications device, such as personal digital assistants (PDA), tablet devices, gaming devices, or media players, for example. In some embodiments, the mobile communication devices 212A-N can execute a specialized application that provides a communication channel between the mobile communication devices 212A-N and the illness detection and tracking computing system 200. Additionally or alternatively, the mobile communication devices 212A-N can execute a web browser application that allows the respective user 222A-N to interface with the illness detection and tracking computing system 200 through web-based communication. In any event, user data 220A-N can be transmitted from the mobile communication devices 212A-N to the illness detection and tracking computing system 200. While the contents of the user data 220A-N can vary based on implementation, in some embodiments, the user data includes a geolocation 224 (as provided by the mobile communication device 212A-N), a user temperature reading 226 (as measured by the temperature sensing probe 214A-N), and a time stamp 228.

Based on the user data 220A-N received from the mobile communication devices 212A-N the illness detection and tracking computing system 200 can generate illness signals 240 that can be provided to various recipient computing systems 242. As is to be appreciated, such illness signals 240 can be provided or otherwise conveyed in any suitable format through dashboards, animations, or a variety of other types of displays. For example, the illness signal(s) 240 can be made available for consumption by external applications or organizations (e.g., public health system) through application programming interfaces (APIs). In one embodiment, for example, the illness detection and tracking computing system 200 can produce illness signal(s) 240 that are indicative of aggregated community influenza levels for each of the geographic regions 218A-N. Additionally or alternatively, such illness signal(s) 240 can indicate the presence of a potential contagious illness outbreak in one or more of the geographic regions 218A-N. In embodiments utilizing other population nodes besides geographic regions, such signal(s) 240 can be generated based on the particular population node being surveilled. As such, the signal(s) can be indicative of outbreak activity within a particular school, school system, institution of higher learning, or a variety of other groupings or collections of users.

The illness detection and tracking computing system 200 can be provided using any suitable processor-based device or system, such as a personal computer, laptop, server, mainframe, or a collection (e.g., network) of multiple computers, for example. The illness detection and tracking computing system 200 can include one or more processors 202 and one or more computer memory units 204. For convenience, only one processor 202 and only one memory unit 204 are shown in FIG. 1. The processor 202 can execute software instructions stored on the memory unit 204. The processor 202 can be implemented as an integrated circuit (IC) having one or multiple cores. The memory unit 204 can include volatile and/or non-volatile memory units. Volatile memory units can include random access memory (RAM), for example. Non-volatile memory units can include read only memory (ROM), for example, as well as mechanical non-volatile memory systems, such as, for example, a hard disk drive, an optical disk drive, etc. The RAM and/or ROM memory units can be implemented as discrete memory ICs, for example.

The memory unit 204 can store executable software and data for the illness detection and tracking computing system 200. When the processor 202 of the illness detection and tracking computing system 200 executes the software, the processor 202 can be caused to perform the various operations of the illness detection and tracking computing system 200. Data used by the illness detection and tracking computing system 200 can be from various sources, such as a database(s) 206, which can be an electronic computer database, for example. The data stored in the database(s) 206 can be stored in a non-volatile computer memory, such as a hard disk drive, a read only memory (e.g., a ROM IC), or other types of non-volatile memory. In some embodiments, one or more databases 206 can be stored on a remote electronic computer system, for example. As is to be appreciated, a variety of other databases, or other types of memory storage structures, can be utilized or otherwise associated with the illness detection and tracking computing system 200. Additionally, the illness detection and tracking computing system 200 can use third party data set(s) 230, as may be provided by various third parties. In some embodiments, the third party data set(s) 230 comprise illness-based web data received from a national public health institute, for example.

As shown in FIG. 3, the illness detection and tracking computing system 200 can include several computer servers and databases. For example, the illness detection and tracking computing system 200 can include one or more application servers 208, web servers 210, and/or any other type of servers. For convenience, only one application server 208 and one web server 210 are shown in FIG. 3, although it should be recognized that the disclosure is not so limited. The servers can cause content to be sent to the mobile computing devices 212A-N and/or other recipient computing systems 242 in any number of formats, such as text-based messages, multimedia message, email messages, smart phone notifications, web pages, and so forth. The servers 208 and 210 can comprise processors (e.g., CPUs), memory units (e.g., RAM, ROM), non-volatile storage systems (e.g., hard disk drive systems), etc. The servers 208 and 210 can utilize operating systems, such as Solaris, Linux, or Windows Server operating systems, for example.

The web server 210 can provide a graphical web user interface through which various users of the system can interact with the illness detection and tracking computing system 200. The web server 210 can accept requests, such as HTTP requests, from clients (such as via web browsers on the mobile computing devices 212A-N, recipient computing system(s) 242, for example), and serve the clients responses, such as HTTP responses, along with optional data content, such as web pages (e.g., HTML documents) and linked objects (such as images, video, and so forth).

The application server 208 can provide a user interface for users who do not communicate with the illness detection and tracking computing system 200 using a web browser. Such users can have special software installed on their mobile computing devices 212A-N, and/or recipient computing system(s) 242 that allows them to communicate with the application server 208 via the communication network 234. Such software can be downloaded, for example, from the illness detection and tracking computing system 200, or other software application provider, over the communication network 234 to such computing devices.

Embodiments of the illness detection and tracking computing system 200 can also be implemented in cloud computing environments. "Cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

Figure 4:
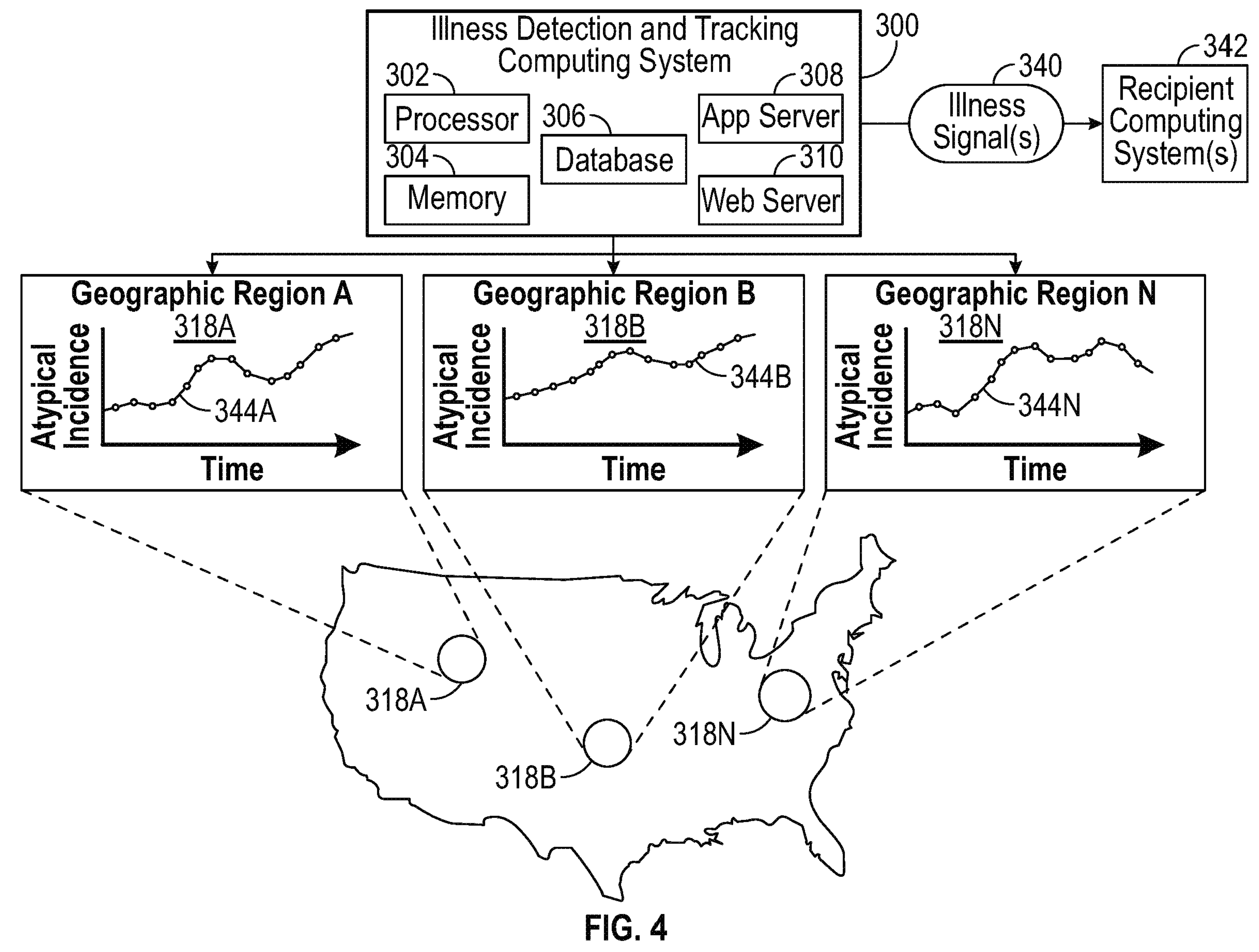

Referring now to FIG. 4, another example illness detection and tracking computing system 300 is depicted. The illness detection and tracking computing system 300 can be similar to the illness detection and tracking computing system 200. As shown, the illness detection and tracking computing system 300 can include, for example, a processor 302, a memory unit 304, a database 306, an application server 308, and a web server 310. The illness detection and tracking computing system 300 can be configured to provide illness signal(s) 340 to various recipient computing systems 342. As shown, the illness detection and tracking computing system 300 can generate, for example, atypical illness reporting for each of a plurality of geographic regions 318A-N. For the purposes of illustration, atypical illness rates for each atypical illness geographic region 318A-N, as determined by the illness detection and tracking computing system 300, are shown as plots 344A-N. As used herein, atypical illness can refer to the difference between the real-time thermometer ILI signal and the 97.5% percentile drawn from an influenza forecast ensemble. As is to be appreciated, however, other percentiles and/or other approaches for quantifying atypical illness can be used without departing from the scope of the present disclosure.

The geographic regions 318A-N can be any suitable region, such as a county, a zip code, a state, a country, a metropolitan statistical area (MSA), and so forth. While geographic regions 318A-N are depicted in FIG. 4 for the purposes of illustration, it is to be appreciated that the illness detection and tracking computing system 300 can generate signaling for a variety of different types of population nodes.

Figure 5:
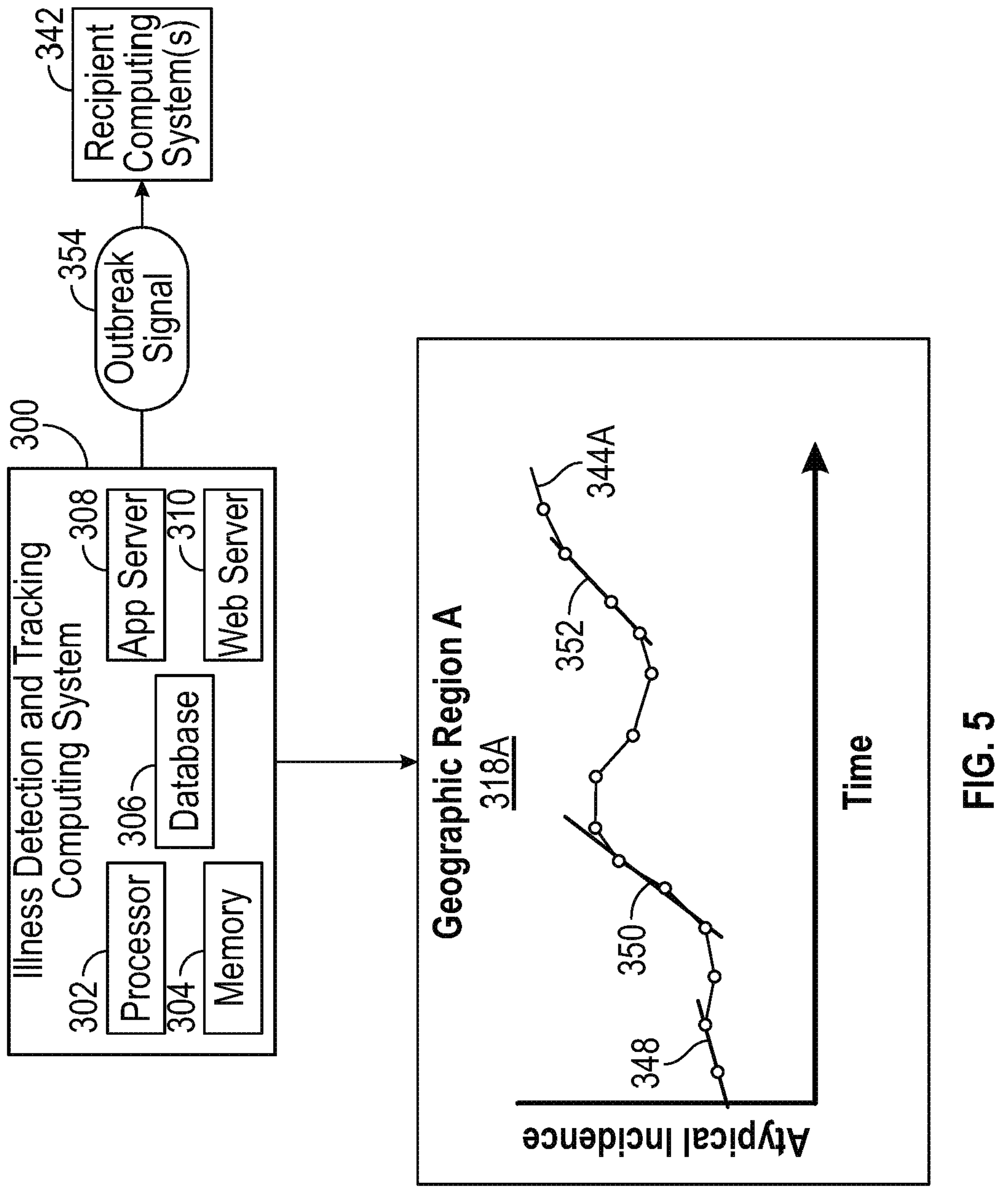
FIG. 5 schematically illustrates detection of a contagious illness outbreak for a geographic region in accordance with one non-limiting embodiment.

Referring now to FIG. 5, detection of a contagious illness outbreak for geographic region 318A by the illness detection and tracking computing system 300 is schematically illustrated. Determined rates of change 348, 350, 352 of fever-induced illness for geographic region 318A are schematically shown. As is to be appreciated, when the determined rate of change increases, the number of atypical incidences over a period of time are rising. As such, when the determined rate of change of fever-induced illness exceeds a threshold rate of change, an outbreak signal 354 can be generated by the illness detection and tracking computing system 300. Additionally, based on the determined rates of change 348, 350, 352, the illness detection and tracking computing system 300 can be used to determine an effective reproduction rate (Rt). As used herein, reproductive rate (Rt) is defined as the average number of secondary cases of febrile disease caused by a single febrile individual over their infectious period. Thus the signaling produced by the illness detection and tracking computing system 300 can be used to continuously provide insights into disease outbreaks, such as alerting to likely future case surges or predicting the magnitude and timing of peak cases for a particular population node or grouping of population nodes.

In some embodiments, observed illness, atypical illness, and atypical transmission signals are incorporated by the illness detection and tracking computing system 300 into a classification model that can be used to predict periods of high, continuous contagious illness case growth for particular population nodes. These periods of high case growth can be defined by periods of high day-over-day growth in normalized case counts, determined from the first difference and corresponding to periods of high case accumulation during exponential growth. In accordance with various embodiments, the trained classification models can predict the target at least two weeks in advance. This allows the prediction of outbreak events, providing early warning at various geographic areas or nodes.

Figure 6:
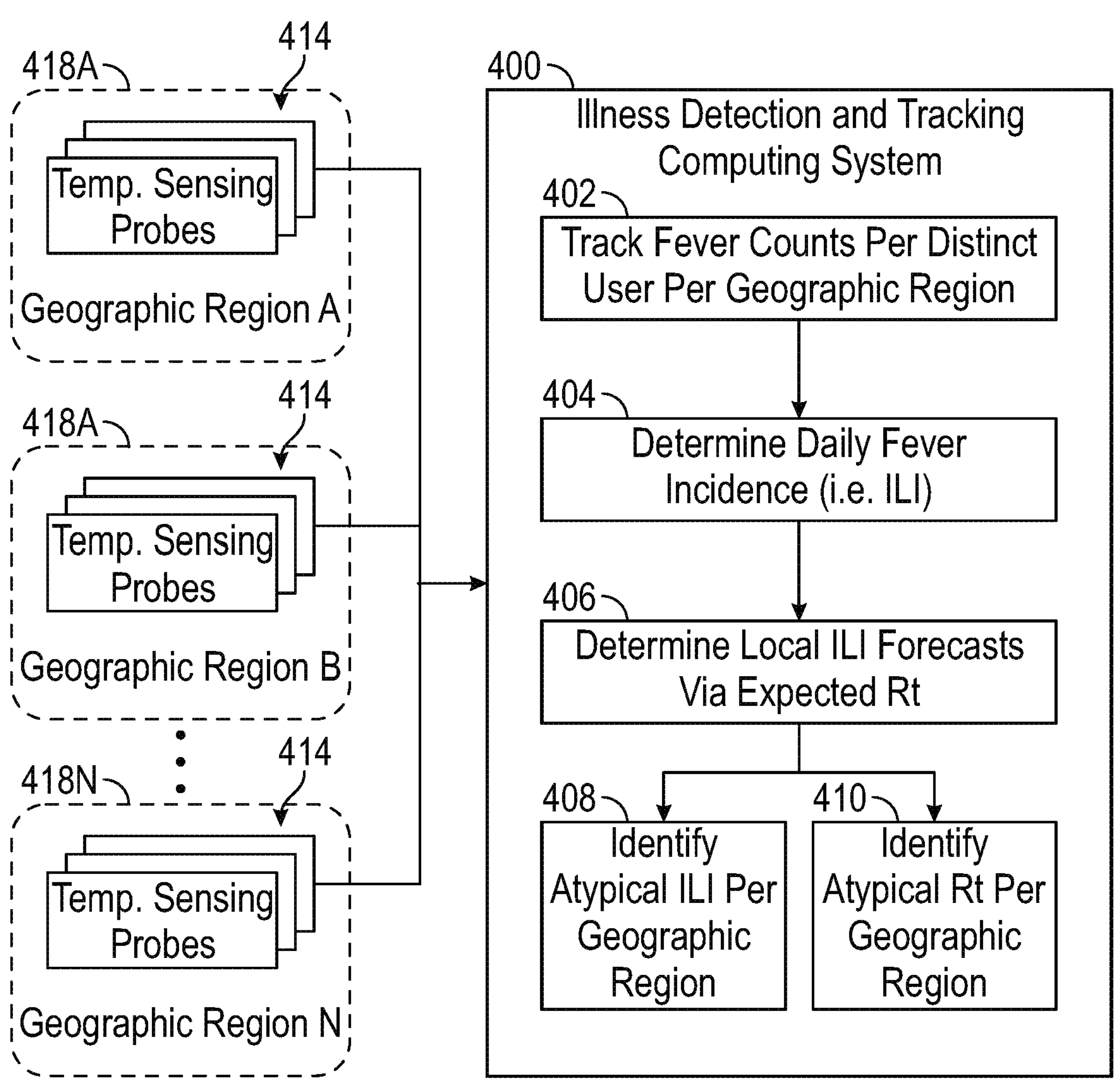
FIG. 6 depicts example processing of information that is received from a plurality of temperature sensing probes by an illness detection and tracking computing system.

Referring now to FIG. 6, example processing of information received from a plurality of temperature sensing probes 414 by an illness detection and tracking computing system 400 is depicted. As shown, the temperature sensing probes 414 can be dispersed amongst a plurality of different population nodes, shown as geographic regions 418A-N for the purposes of illustration. Based on user data received from each of the temperature sensing probes 414 the illness detection and tracking computing system 400 can perform various processing. At 402, the illness detection and tracking computing system 400 can track fever counts per distinct user per each geographic region 418A-N. Furthermore, in some embodiments, other additional symptoms of users can be received by the illness detection and tracking computing system 400. For example, a user can manually enter symptoms into a mobile communication device associated with the temperature sensing probes 414, and the mobile communication device can transmit the symptom listing to the illness detection and tracking computing system 400. At 404, the illness detection and tracking computing system 400 can determine a daily fever incidence level (such as an ILI determination). Next, at 406, the illness detection and tracking computing system 400 can determine ILI forecasts for each geographic region 418A-N. Such ILI forecasts can be based on, for example, the expected Rt for each geographic region. Once the ILI forecast is determined, the illness detection and tracking computing system 400 can then monitor for deviations from the forecast. At 408, the illness detection and tracking computing system 400 can identify an atypical ILI in a particular geographic region 418A-N. At 410, the illness detection and tracking computing system 400 can identify an atypical Rt in a particular geographic region 418A-N. Based on the identification of atypical ILI and/or atypical Rt, appropriate signaling can be generated by the illness detection and tracking computing system 400 and provided to appropriate recipients, such as federal, state, local governments, school officials, and/or healthcare entities for example.

Figure 7:
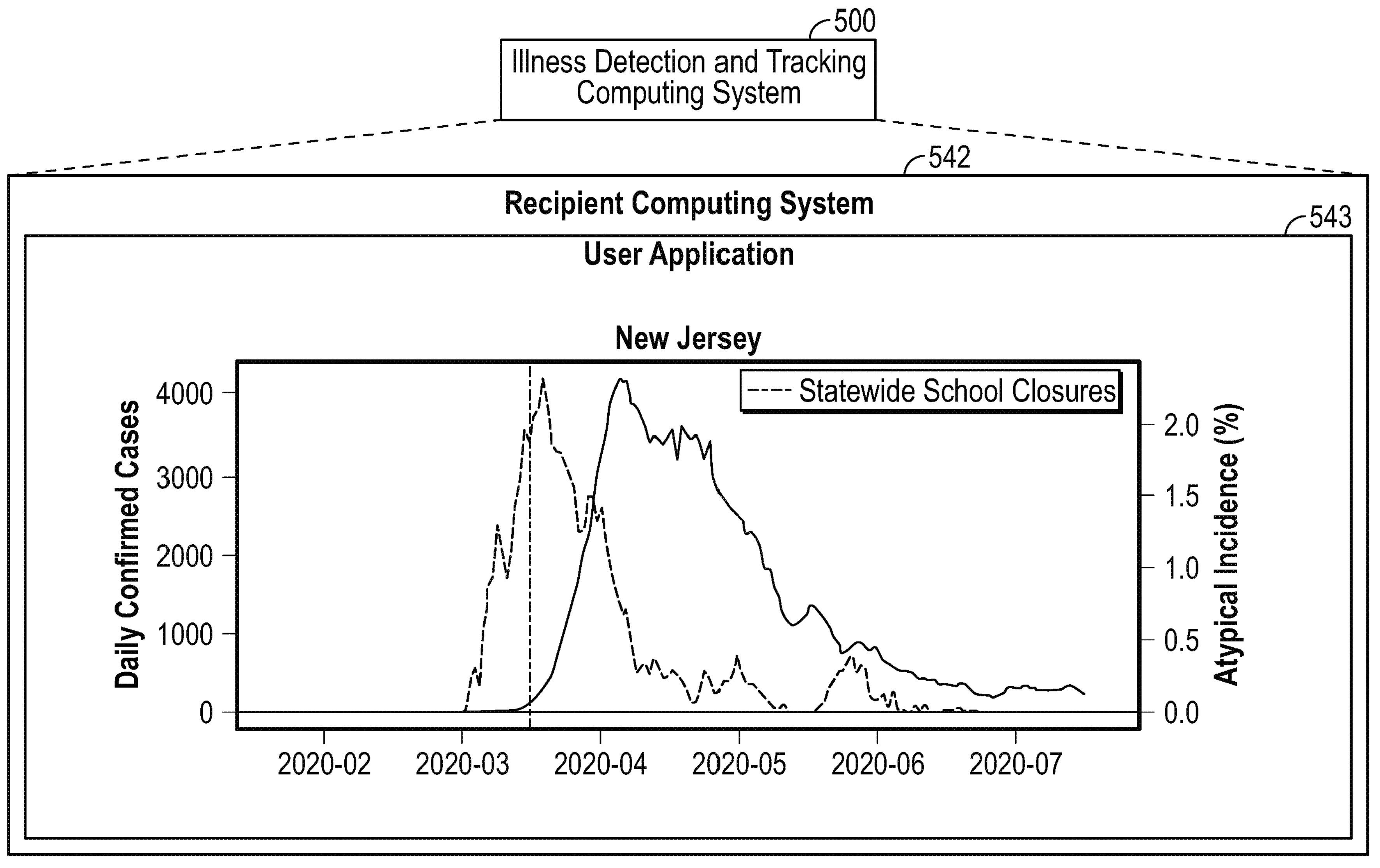
FIGS. 7-9 provide example visualizations generated by an illness detection and tracking computing system in accordance with one non-limiting embodiment.

FIG. 7 provides an example visualization 543 generated by an illness detection and tracking computing system 500 that can be presented on a recipient computing system 542. As is to be appreciated, the illness detection and tracking computing system 500 can be in communication with a plurality of mobile computing devices, each of which are in communication with a smart thermometer (as shown in FIG.

3, for example). The visualization 543 conveys atypical incidence (dashed line) over time and daily confirmed cases of COVID-19 (solid line) over the same time period. In this illustrated example, the population node is a geographic region. As shown by the visualization 543, the illness detection and tracking computing system 500 successfully detected the surge in daily confirmed cases in the state of New Jersey over two weeks prior to occurrence of the surge. Thus, the illness detection and tracking computing system 500 can be leveraged to accurately detect community spread of contagious illness approximately 2-4 weeks in advance of laboratory confirmed case surges, depending on laboratory capacity and test availability. Beneficially, the illness detection and tracking computing system 500 can provide resolution to the county and even sub-county level in areas with high thermometer penetration. Based on the valuable information and alerts provided by the illness detection and tracking computing system 500 actions can be taken, such as the closure of schools, social distancing mandates, and the like, in an effort to reduce the impacts of the pending surge. Additionally, testing kits, medicines, and so forth, can be efficiently managed in view of the surges identified by the illness detection and tracking computing system 500.

Figure 8:
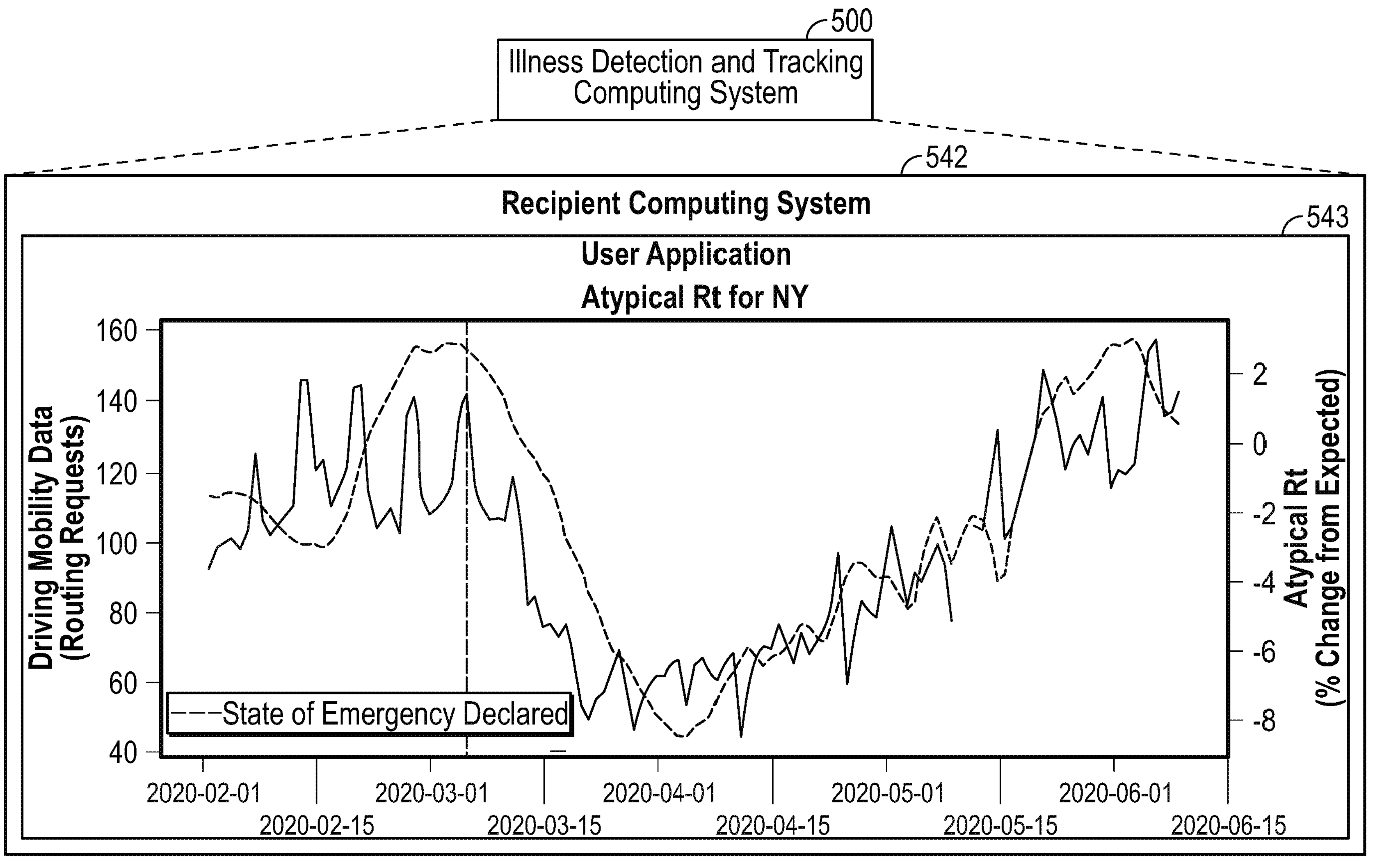

FIG. 8 provides another example visualization 543 generated by the illness detection and tracking computing system 500 and presented on the recipient computing system 542. In this example visualization 543, the impact of mobility restrictions on a population over a period of time can be assessed based on the determined change of atypical Rt over the period of time. In the illustrated example for New York, the number of routing requests to mapping websites is plotted over time (solid line), with a state of emergency declared on Mar. 7, 2020. Subsequent to the declaration of the state of emergency, the number of routing requests declines as the number of drivers decrease. Correlated to the declaration of the state of emergency, the atypical Rt (dashed line) is also shown to similarly decline, thereby confirming that the mobility restrictions beneficially impacted Rt for New York.

Figure 9:
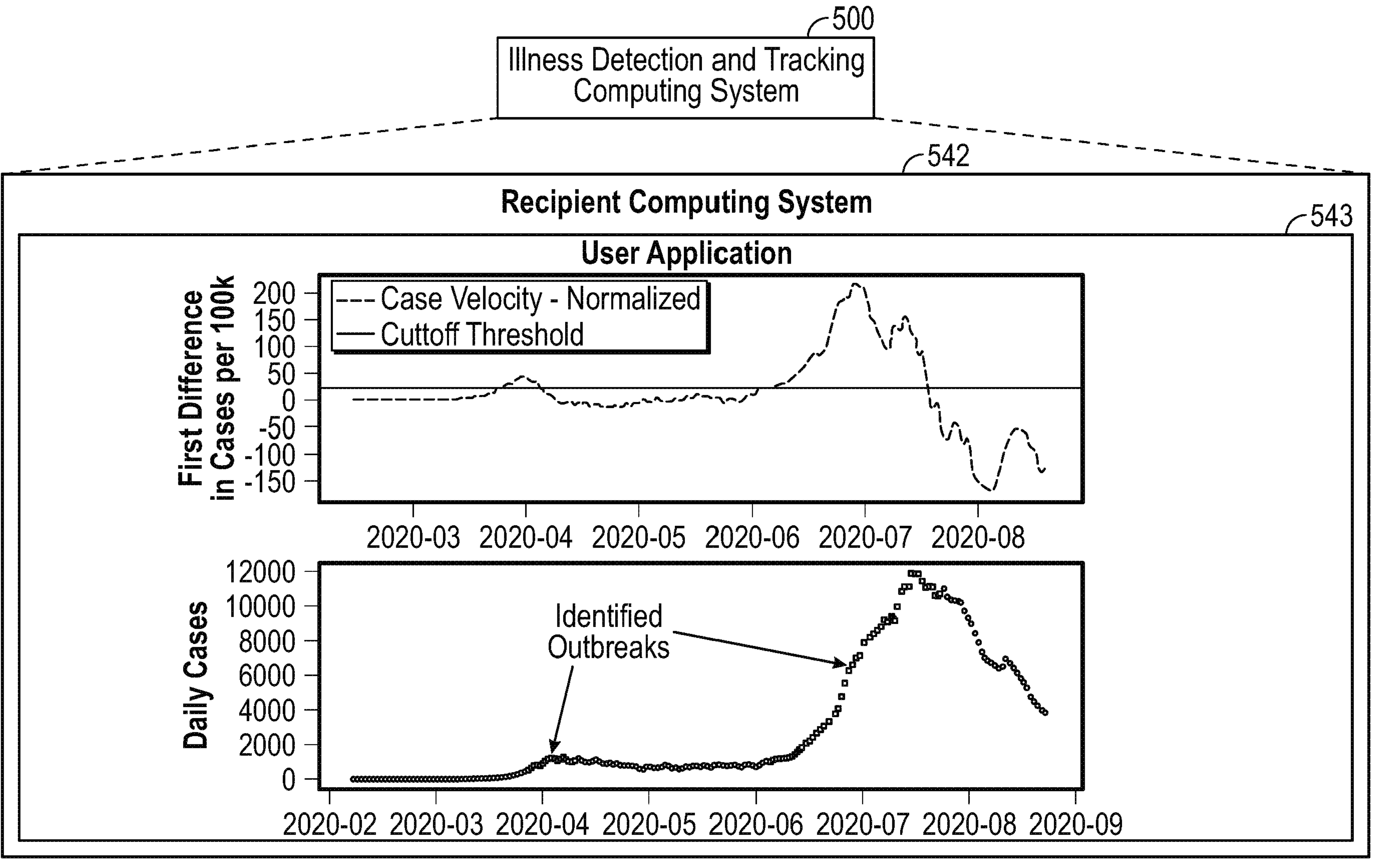

FIG. 9 provides another example visualization 543 generated by the illness detection and tracking computing system 500 and presented on the recipient computing system 542. In this example visualization 543, the normalized case velocity over time (dashed line), as determined by the illness detection and tracking computing system 500, is shown in the top plot. Additionally, a cutoff threshold velocity (solid line) is plotted. The crossing of the normalized case velocity above the cutoff threshold velocity is indicative of a rapid increase in cases. Based on this threshold crossing, appropriate outbreak signaling can be generated. The bottom plot includes the number of daily confirmed cases over the same period of time, with outbreaks identified. As shown, the identified outbreaks are correlated to points in time that the normalized case velocity exceeded the cutoff threshold.

FIG. 10 is a flow chart of an example process that can be performed by an illness detection and tracking computing system in accordance with the present disclosure. At 602, user data from each of a plurality of mobile computing devices is received by the illness detection and tracking computing system via network communications over a period of time. The user data received from each of the computing devices can comprise a geolocation of the computing device, a user temperature reading as collected by the associated temperature sensing probe, and a time stamp associated with the temperature reading. At 604, for each of the plurality of different geographic regions, and based on the user data received from the mobile computing devices physically located within each of the different geographic regions, a rate of change of fever-induced illness can be determined based on the user data. At 606, an illness signal is generated for each of the different geographic regions based on the determined rate of change of fever-induced illness for each of the different geographic regions. At 608, the illness signal for each of the different geographic regions is graphically conveyed. The illness signal can be a real-time illness signal. At 610, it is determined if the rate of change of fever-induced illness for each of the different geographic regions is above a threshold rate of change. If so, at 612, an outbreak signal can be generated for the associated geographic region, or other suitable population node. Otherwise, the process can progress to 614, where an effective reproduction rate (Rt) can be determined for each of the different geographic regions based at least in part on the determined rate of change of fever-induced illness for each of the different geographic regions.

The foregoing description of embodiments and examples has been presented for purposes of description. It is not intended to be exhaustive or limiting to the forms described. Numerous modifications are possible in light of the above teachings. Some of those modifications have been discussed and others will be understood by those skilled in the art. The embodiments were chosen and described for illustration of various embodiments. The scope is, of course, not limited to the examples or embodiments set forth herein, but can be employed in any number of applications and equivalent articles by those of ordinary skill in the art.

What is claimed is:

1. An illness detection and tracking system, comprising:

a plurality of biometric collection devices, wherein each of the plurality of biometric collection devices are configured to communicate with an associated mobile computing device, and wherein the plurality of biometric collection devices are dispersed amongst a plurality of population nodes;

a computing system comprising at least one memory and at least one processor, wherein the computing system is in networked communication with each of the mobile computing devices, wherein the at least one memory stores instructions which when executed by the at least one processor cause the computing system to:

over a period of time receive user data from each of over five hundred mobile computing devices via network communications, wherein the user data received from each of the over five hundred mobile computing devices comprises a user temperature reading as collected by the associated biometric collection devices;

for each of the plurality of population nodes, based on the user data received over the period of time from the mobile computing devices associated with the respective population node, determine a rate of change of fever-induced illness based on the user data received from the mobile computing devices associated with the respective population node;

generate an illness signal for at least one of the plurality of population nodes based on the determined rate of change of fever-induced illness for at least one of the plurality of population nodes; and provide the generated illness signal for the at least one of the plurality of population nodes to a third-party recipient.

2. The illness detection and tracking system of claim 1, wherein the generated illness signal is a real-time illness signal.

3. The illness detection and tracking system of claim 1, wherein the instructions further cause the computing system to:

generate a first illness signal for a first population node of the plurality of population nodes; and generate a second illness signal for a second population node of the plurality of population nodes.

4. The illness detection and tracking system of claim 1, wherein the instructions further cause the computing system to determine an effective reproduction rate (Rt) for each the plurality of population nodes.

5. The illness detection and tracking system of claim 1, wherein the instructions further cause the computing system to receive data sets from one or more third parties via network communications.

6. The illness detection and tracking system of claim 1, wherein the plurality of biometric collection devices are any one of a pulse oximeter, a heart rate monitor, a wearable fitness tracker, a temperature sensing probe, and a wearable device.

7. The illness detection and tracking system of claim 1, wherein the mobile computing devices are any one of a smart phone, a tablet computer, a laptop computer, and a desktop computer.

8. The illness detection and tracking system of claim 1, wherein one or more of the plurality of population nodes is a geographic region, and wherein the mobile computing devices associated with the geographic region are physically located within the geographic region.

9. The illness detection and tracking system of claim 1, wherein one or more of the plurality of population nodes is a geographic region and the geographic region is a state, and wherein the mobile computing devices associated with the geographic region are physically located within the state.

10. The illness detection and tracking system of claim 1, wherein one or more of the plurality of population nodes is any one of a school, a school system, or an institution of higher learning.

11. The illness detection and tracking system of claim 1, wherein the instructions further cause the computing system to:

compare the determined rate of change of fever-induced illness for each of the plurality of population nodes to a threshold rate of change; and when the determined rate of change of fever-induced illness exceeds the threshold rate of change, generate an outbreak signal for the associated population node.

12. A computing system comprising at least one memory and at least one processor, wherein the computing system is in networked communication with each of a plurality of mobile computing devices, wherein the at least one memory stores instructions which when executed by the at least one processor cause the computing system to:

over a period of time receive user data from each of over five hundred mobile computing devices via network communications, wherein the user data received from each of the over five hundred mobile computing devices comprises a user temperature reading as collected by a biometric collection device associated with the respective mobile computing device;

for each of a plurality of population nodes, based on the user data received over the period of time from the mobile computing devices associated with the respective population node, determine a rate of change of fever-induced illness based on the user data received from the mobile computing devices associated with the respective population node;

generate an illness signal for at least one of the plurality of population nodes based on the determined rate of change of fever-induced illness for each of the population nodes; and provide the generated illness signal for the at least one of the plurality of population nodes to a third-party recipient.

13. The computing system of claim 12, wherein the generated illness signal is a real-time illness signal.

14. The computing system of claim 12, wherein the instructions further cause the computing system to determine an effective reproduction rate (Rt) for each the plurality of population nodes.

15. The computing system of claim 12, wherein the biometric collection devices are any one of a pulse oximeter, a heart rate monitor, a wearable fitness tracker, a temperature sensing probe, and a wearable device.

16. The computing system of claim 12, wherein the plurality of mobile computing devices are any one of a smart phone, a tablet computer, a laptop computer, and a desktop computer.

17. The computing system of claim 12, wherein one or more of the plurality of population nodes is a geographic region, and wherein the mobile computing devices associated with the geographic region are physically located within the geographic region.

18. The computing system of claim 12, wherein one or more of the plurality of population nodes is any one of a school, a school system, or an institution of higher learning.

19. The computing system of claim 12, wherein the instructions further cause the computing system to:

compare the determined rate of change of fever-induced illness for each of the population nodes to a threshold rate of change; and when the determined rate of change of fever-induced illness exceeds the threshold rate of change, generate an outbreak signal for the associated population node.

20. An illness detection and tracking method, comprising:

receiving, by a computing system, a threshold biometric rate of change for a population node;

receiving, by the computing system, user data collected from over five hundred biometric collection devices, wherein the user data received from each of the over five hundred biometric collection devices comprises a biometric reading for a user as collected by the one or more biometric collection devices;

storing the user data collected from the over five hundred biometric collection devices in a data store, wherein the user of each biometric collection device is a member of the population node;

based on the user data in the data store, determining, by the computing system, a biometric rate of change for the population node;

comparing, by the computing system, the determined biometric rate of change for the population node to the threshold rate of change for the population node;

when the determined real-time biometric rate of change exceeds the threshold rate of change for the population node, generating, by the computing system, an illness signal for the population node; and providing, by the computing system, the illness signal to a third-party application via network communications through an application programming interface.

* * * * *